US012758560B2

(12) United States Patent
Mehra

(10) Patent No.: US 12,758,560 B2
(45) Date of Patent: Oct. 13, 2026

(54) METHODS AND COMPOSITIONS FOR THE TREATMENT OF TRAUMATIC BRAIN INJURY (TBI) AND RELATED DISORDERS

(71) Applicant: Akhil Mehra, San Francisco, CA (US)

(72) Inventor: Akhil Mehra, San Francisco, CA (US)

( * ) Notice: Subject to any disclaimer, the term of this patent is extended or adjusted under 35 U.S.C. 154(b) by 618 days.

(21) Appl. No.: 18/364,675

(22) Filed: Aug. 3, 2023

(65) Prior Publication Data

US 2023/0381195 A1 Nov. 30, 2023

Related U.S. Application Data

(63) Continuation-in-part of application No. 16/956,043, filed as application No. PCT/US2018/066286 on Dec. 18, 2018, now abandoned.

(60) Provisional application No. 62/608,105, filed on Dec. 20, 2017.

(51) Int. Cl.
*A61K 31/55* (2006.01)
*A61K 9/70* (2006.01)
*A61K 45/06* (2006.01)

(52) U.S. Cl.
CPC .............. *A61K 31/55* (2013.01); *A61K 9/703* (2013.01); *A61K 45/06* (2013.01)

(58) Field of Classification Search
CPC ...... A61K 31/138; A61K 31/55; A61K 9/703; A61K 9/7084
See application file for complete search history.

(56) References Cited

FOREIGN PATENT DOCUMENTS

WO WO-2009069126 A1 * 6/2009 .............. A61P 43/00
WO WO-2016042413 A1 * 3/2016 .............. A61P 25/08

OTHER PUBLICATIONS

Blennow et. al., Lancet, vol. 368, pp. 387-403, publ. 2006 (Year: 2006).*
Rathbone et. al., Brain, Behavior, & Immunity, vol. 46, pp. 1-16, publ. 2015 (Year: 2015).*

* cited by examiner

*Primary Examiner* — Sarah Pihonak
(74) *Attorney, Agent, or Firm* — Jenei LLC

(57) ABSTRACT

The present invention relates to methods for the treatment or prevention of symptoms associated with traumatic brain injury (TBI) and related disorders. The present disclosure provides compositions and methods for preventing, ameliorating, or alleviating neuropsychiatric symptoms and psychiatric disorders associated with TBI and related disorders consisting of administering a matrix-type transdermal patch with a composition consisting of opipramol, excluding any other component such as a pharmaceutical carrier or excipient.

9 Claims, No Drawings

METHODS AND COMPOSITIONS FOR THE TREATMENT OF TRAUMATIC BRAIN INJURY (TBI) AND RELATED DISORDERS

CROSS-REFERENCE TO RELATED APPLICATIONS

The present application is a continuation-in-part of U.S. Nonprovisional application Ser. No. 16/956,043, filed Jun. 19, 2020, which claims priority to PCT Application No. PCT/US18/66286, filed Dec. 18, 2018, which claims priority to U.S. Provisional Application No. 62/608,105 filed Dec. 20, 2017; which applications are herein incorporated by reference for all purposes.

TECHNICAL FIELD

The present invention relates to methods for the treatment or prevention of symptoms associated with traumatic brain injury (TBI) and related disorders. The present disclosure provides compositions and methods for preventing, ameliorating, or alleviating neuropsychiatric symptoms and psychiatric disorders associated with TBI and related disorders consisting of administering a matrix-type transdermal patch with a composition consisting of opipramol, excluding any other component such as a pharmaceutical carrier or excipient.

BACKGROUND

Traumatic brain injury (TBI) is a disorder of variable etiology and severity. It is classified as mild (concussion), moderate and severe in intensity. TBI is a major cause of death and morbidity internationally. There are approximately 1.7 million cases in the USA annually. There also are approximately 2.4 million emergency department visits, with nearly one-third of all injury-deaths including a diagnosis of TBI. In addition, approximately 5.3 million U.S. residents are living with a disability related to TBI. The total economic cost of TBI is estimated to be 76.5 billion annually. Besides athletes and members of the armed forces, the larger civilian population is at significant TBI risk from motor vehicle crashes, falls, assault, blunt impact and other unknown factors.

Opipramol is a tricyclic compound with the nucleus of the anticonvulsant carbamazepine and the side chain of the neuroleptics fluphenazine and perphenazine without reuptake inhibiting properties for serotonin (5-HT) or noradrenaline. In vitro, it blocks the following receptors in decreasing order: histamine (H1.H2), serotonin (5-HT2), dopamine (D2.D1), adrenergic (al), and very weakly cholinergic receptors. The blocking potential for H1, 5-HT2 and D2 receptors places opipramol between the classical antidepressants, atypical neuroleptics and anxiolytics (classical sedatives as well as serotonergic antagonists in the developmental state). Recent basic research also characterized opipramol as a strong sigma ligand with complex interactions on the dopaminergic system and the NMDA receptor complex. It also induces increased levels of cGMP and it possesses anti-ischemic effects.

Opipramol was originally developed in the sixties as an antidepressant, its anxiolytic properties were soon recognized and have recently been confirmed in a well-designed clinical trial in patients with generalized anxiety disorders, demonstrating superiority over placebo and similar efficacy to alprazolam.

There is therefore a need in the art for the discovery of additional methods for the treatment or prevention of symptoms associated with traumatic brain injury (TBI) and related disorders. The present disclosure describes compositions and methods of preventing, ameliorating, or alleviating neuropsychiatric symptoms and psychiatric disorders associated with TBI and related disorders consisting of administering a matrix-type transdermal patch with a composition consisting of opipramol, excluding any other component such as a pharmaceutical carrier or excipient.

SUMMARY OF THE INVENTION

Compositions and methods for the treatment or prevention of symptoms associated with traumatic brain injury (TBI) and related disorders, are provided. The present invention relates to compositions and methods for preventing, ameliorating, or alleviating neuropsychiatric symptoms and psychiatric disorders associated with TBI and related disorders consisting of administering a matrix-type transdermal patch with a composition consisting of opipramol, excluding any other component such as a pharmaceutical carrier or excipient.

A method for preventing, ameliorating or alleviating neuropsychiatric symptoms and psychiatric disorders associated with traumatic brain injuries (TBI) and related disorder consisting of administering to a human in need of such treatment by a matrix-type transdermal patch with a composition consisting opipramol in an amount effective to prevent, ameliorate or alleviate one or more symptoms of the traumatic brain injuries (TBI) related disorder, wherein the opipramol is administered in a symptom reducing effective dosage of ranges: from 5-500 mg per day, from 25 to 450 mg per day, from 40 to 450 mg per day, from 50 to 400 mg per day, from 50 to 300 mg per day, from 100 to 300 mg per day, from 150 to 300 mg per day, wherein the transdermal patch results in a 20-50% bioavailability increase, a 50%-100% increase, up to a three-fold, or greater increase, and a five-fold or greater increase in bioavailability compared to that obtained with an equivalent oral dosage form, and wherein the disorder is selected from the group consisting of traumatic brain injury (TBI), concussion, sport-related concussion, post-concussion syndrome, open head injury, closed head injury, contusion, diffuse axonal injury, coup-contre coup injury, second impact syndrome, penetrating injury, shaken baby syndrome, locked in syndrome, anoxic brain injury, hypoxic brain injury and Alzheimer's disease, Parkinson's disease, Huntington's disease, and ALS, wherein the method further consisting coordinately administering (a) one or more additional therapeutic agent in an amount effective to prevent, ameliorate or alleviate one or more symptoms of the disorder, (b) coordinately administering one or more non-pharmacological treatments effective to prevent, ameliorate or alleviate one or more symptoms of the disorder, or (c) both, and the one or more additional therapeutic agent is selected from the group consisting of anti-depressant, mood-stabilizing, anxiolytic, anticonvulsant, stimulant, antipsychotic, antiaddictive, appetite suppressant drugs and opiate agonists.

In one aspect of the invention, the neuropsychiatric symptoms and psychiatric disorders comprise one of more of the following 1) neurotic symptoms: headache, vertigo, dizziness, fatiguability, listlessness, pain, weakness, hypochondria, anxiety, irritability, 2) mood disorders: dysphoria, dysthymia, depressive mood, agitation, euphoria, hypomanic mood, flattening of affect, sleep disorders, 3) behaviors: apathy, psychomotor retardation, subjective work difficulties, 4) cognitive impairment: forgetting location of objects, decreased functioning in demanding employment settings, and difficulty in traveling to new locations. (5) agitation and aggression, disinhibition, disinhibition of sexual behavior, psychotic symptoms including delusions, hallucinations, ideas or reference, paranoia, erotomanic delusions, confabulation, amnesia, paramnesia, fregoli syndrome, impulse control problems, intermittent explosivity, conduct problems, behavioral dysregulation, language problems, intellectual gambling, kleptomania, pyromania, trichotillomania, trauma and stressor related symptoms, nightmares, repeated, disturbing memories, thoughts, or images of a stressful experience from the past, repeated, disturbing dreams of a stressful experience from the past, suddenly acting or feeling as if a stressful experience were happening again, feeling very upset with a reminder of a stressful experience from the past, having physical reactions when reminded of a stressful experience from the past, avoiding thinking about or talking about a stressful experience from the past or avoid having feelings related to it, avoiding activities or situations because of a stressful experience from the past, trouble remembering important parts of a stressful experience from the past, loss of interest in previously pleasurable activities, feeling distant or cut off from other people, feeling emotionally numb or being unable to have loving feelings, feeling as if one's future will somehow be cut short, trouble falling or staying asleep, feeling irritable or having angry outbursts, having difficulty concentrating, being "super alert" or watchful on guard, feeling jumpy or easily startled, memory loss (amnesia) of certain time periods, events, people and personal information, a sense of being detached from oneself and one's emotions, a perception of the people and things around as distorted and unreal, a blurred sense of identity, feeling in a daze, during or after the trauma, feeling unreal or dreamlike, during or after the trauma, feeling distant from one's normal self or like one were watching it happen from outside, being unable to recall important aspects of the trauma, having memories of the trauma kept that entering one's mind, having bad dreams or nightmares about the trauma, having felt as if the trauma was about to happen again, feeling upset when you reminded of the trauma, trying not to think about the trauma trying not to talk about the trauma, avoiding situations or people that remind one of the trauma, trying not to feel upset or distressed about the trauma, having trouble sleeping since the trauma, feeling more irritable since the trauma, difficulty concentrating since the trauma, become more alert to danger since the trauma, when reminded of the trauma, sweating or heart beating fast, I feel more nervous and anxious than usual, feeling afraid for no reason at all, getting upset easily or feeling panicky, feeling like one is falling apart and going to pieces, feeling that everything is all bad and nothing right will happen, arms and legs that shake and tremble, headaches neck and back pain, feeling weak and getting tired easily, dizzy spells, fainting spells, trouble breathing easily, feelings of numbness and tingling in fingers & toes, stomach aches or indigestion, having to empty one's bladder often, hands feeling usually dry and warm, face getting hot and blushing, self-injurious behavior, substance use disorders, phobias, homicidal ideation, and suicidal ideation.

In one aspect of the invention, the opipramol is administered prior to a brain injury (TBI) related disorder. In another aspect, the opipramol is administered after a brain injury (TBI) related disorder. Still, in another aspect, the opipramol is administered after development of symptoms of the traumatic brain injury (TBI) related disorder.

In one aspect of the invention, one or more additional therapeutic agent is an anti-depressant drug selected from the group consisting of tri-cyclic anti-depressants (TCAs), specific monoamine reuptake inhibitors, selective serotonin reuptake inhibitors (SSRIs), selective norepinephrine reuptake inhibitors, selective dopamine reuptake inhibitors, multiple monoamine reuptake inhibitors, monoamine oxidase inhibitors (MAOIs), or indeterminate (atypical) anti-depressants.

In one aspect of the invention, the one or more additional therapeutic agent is selected from the group consisting of amantadine, prazosin, propranolol, Alprazolam, Ambien, Ambien CR, amitriptyline, Amphetamine, Amytal Sodium (amobarbital sodium), Amytriptiline, aripiprazole, asenapine, atorvastatin, brexipiprazole, Bromocriptine, bupropion, buspirone, Butisol (butabarbital sodium), Carbamazepine (Tegretol), Carbidopa, Chlorpromazine, ciclosporin A, Citalopram, Clonazepam, clonidine, Dalmane (flurazepam), desipramine, Desvenlafaxine, dextroamphetamine, donepezil, Doral (quazepam), duloxetine, escitalopram (Lexapro), fluoxetine, fluphenazine, fluvoxamine (Luvox), gabapentin, Galantamine, gepirone, Halcion (triazolam), Haloperidol, iloperidone, Imidazopyridines, imipramine (Tofranil), Intermezzo (zolpidem), isocarboxazid (Marplan), Lamotrigine (Lamictal), Levodopa, levomilnacipran, Lisdexamfetamine Dimesylate, Lodosyn (carbidopa-levodopa), Lorazepam, Lunesta (eszopiclone), lurasidone, Mebaral (mephobarbital), melatonin receptor stimulator, memantine, Methylphenidate, Mirapex (pramipexole), Mirtazapine, moclobemide, nefazodone, Nembutal (phenobarbital), nortriptyline, Notec (chloral hydrate), Nuvigil (armodafinil), olanzapine, omega-3 fatty acids, Oxcarbazepine (Trileptal), paliperidone, Parlodel (bromocriptine mesylate), Paroxetine, Permax (pergolide mesylate), perphenazine (Triavil), phenelzine (Nardil), Pindolol, Precedex (dexmedetomidine hydrochloride), pregabalin, progesterone, Prosom (estazolam), protriptyline, Provigil (modafinil), pyritinol, quetiapine, rasagiline (Azilect), Requip, Requip XL (ropinirole Hcl), Restoril (temazepam), risperidone, Rivastigmine, Rozerem (ramelteon), Seconal Sodium Pulvules (secobarbital sodium), selegiline (Eldepryl, Zelapar), sertraline, simvastatin, Sinemet, Sinemet CR, sodium valproate (Depacon, Epilim), Sonata (pyrazolopyrimidine), Suvorexant (Belsomra), topiramate, transexamic acid, tranylcypromine (Parnate), trazodone, trimipramine (Surmontil), Valium (diazepam), valproate semisodium (Depakote), Valproic acid (Depakine), Venlafaxine, vilazodone (Viibryd), vortioxetine (Trintellix), Xyrem (sodium oxybate) and ziprasidone.

In one aspect a transdermal matrix patch or transdermal semisolid formulation containing for example, pharmaceutical agents, such as opipramol and one or more additional therapeutic agent (e.g., an anti-depressant, mood-stabilizer, anxiolytic, anticonvulsant, stimulant, antipsychotic, anti-addictive, appetite suppressant drugs and opiate agonists), and derivatives of these compounds can be prepared. In another aspect, two separate transdermal matrix patches can be prepared with one containing pharmaceutical agent alone and a second containing another pharmaceutical agent alone as active ingredient. In this case both transdermal matrix patches could be applied at the same time and deliver pharmaceutical agent. In yet another exemplary aspect two separate transdermal semisolid formulations can be prepared one containing pharmaceutical agent alone and a second containing pharmaceutical agent alone as active ingredient.

Moreover, the current disclosure is developing transdermal matrix patches which can deliver pharmaceutical agents, such as opipramol and one or more additional therapeutic agent (e.g., an anti-depressant, mood-stabilizer, anxiolytic, anticonvulsant, stimulant, antipsychotic, anti-addictive, appetite suppressant drugs and opiate agonists), for 1 day, and/or 2-days, and/or 3-days, and/or 4 days, and/or 5 days, and/or 6 days, and/or 7 days, and/or up to 15 days.

The disclosure provides a transdermal and/or topical pharmaceutical composition formulated as transdermal liquid formulation, transdermal semi solid formulation, transdermal gel formulation, or transdermal polymer matrix formulation, transdermal adhesive matrix formulation, transdermal film forming gel, transdermal film forming spray formulation, a multilayer transdermal matrix system, or transdermal drug-in-adhesive matrix formulation.

The disclosure provides a transdermal and/or topical pharmaceutical composition formulated as a topical liquid formulation, topical semisolid formulation, topical gel formulation, topical polymer matrix formulation, topical adhesive matrix formulation, topical film forming gel formulation, or topical film forming spray formulation.

The disclosure provides a transdermal and/or topical pharmaceutical composition formulated as a transdermal patch, wherein the transdermal patch is selected from the group consisting of a reservoir patch, a microreservoir patch, a micro-dosing patch, a matrix patch, a drug in adhesive patch, a pressure sensitive adhesive patch, extended-release transdermal film a liquid reservoir system, a microreservoir patch, a mucoadhesive patch, multilayer transdermal matrix system, and combinations thereof.

The disclosure provides a transdermal and/or topical pharmaceutical composition formulated as a topical patch, wherein the topical patch is selected from the group consisting of a reservoir patch, a microreservoir patch, a matrix patch, a drug in adhesive patch, a pressure sensitive adhesive patch, extended-release transdermal film a liquid reservoir system, a microreservoir patch, a mucoadhesive patch, a micro-dosing patch, multilayer transdermal matrix system, and combinations thereof.

The disclosure provides a transdermal and/or topical pharmaceutical composition formulated as a liquid formulation, transdermal semisolid formulation, or transdermal polymer matrix formulation, transdermal adhesive matrix formulation, film forming gel formulation, film forming spray formulation.

The disclosure provides a transdermal and/or topical pharmaceutical composition further comprising carriers or ingredients in effective amount selected from the group consisting of solvents, gelling agents, polymers, pressure sensitive adhesive polymers, penetration enhancers, emollients, skin irritation reducing agents, buffering agents, pH stabilizers, solubilizers, suspending agents, dispersing agents, stabilizers, plasticizers, tackifiers, diluents, bulking agents, surfactants, antioxidants, oxidants, and combinations thereof in the range of 0.1%-99.5% w/w or w/v.

These and other features are explained more fully in the embodiments illustrated below. It should be understood that in general the features of one embodiment also may be used in combination with features of another embodiment and that the embodiments are not intended to limit the scope of the invention. Other features and advantages of the invention will become apparent from the following detailed description, taken in conjunction with the accompanying drawings, which illustrate, by way of example, various embodiments of the invention.

DETAILED DESCRIPTION OF EXAMPLE EMBODIMENTS

Definitions

As used herein, an "active therapeutic agent" of the present invention includes opipramol and optionally includes one or more other psychotherapeutic compound.

The term "administration" or "administering" includes routes of introducing the compounds, or a composition thereof, of the invention to a subject to perform their intended function. Examples of routes of administration that may be used include injection (subcutaneous, intravenous, parenterally, intraperitoneally, intrathecal), oral, inhalation, rectal and transdermal. The pharmaceutical compositions may be given by forms suitable for each administration route. For example, these compositions are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, a compound described herein can be coated with or disposed in a selected material to protect it from natural conditions which may detrimentally affect its ability to perform its intended function. A compound or composition described herein can be administered alone, or in conjunction with either another agent as described above or with a pharmaceutically-acceptable carrier, or both. A compound or composition described herein can be administered prior to the administration of the other agent, simultaneously with the agent, or after the administration of the agent. Furthermore, a compound described herein can also be administered in a prodrug form which is converted into its active metabolite, or more active metabolite in vivo.

The terms "carrier" or "vehicle" as used herein refer to carrier materials suitable for transdermal drug administration. Contemplated carriers and/or vehicles include any such materials known in the art, which are substantially nontoxic and/or do not interact with other components of a pharmaceutical formulation or drug delivery system in a deleterious manner. Examples of specific suitable carriers and vehicles for use herein include water, propylene glycol, mineral oil, silicone, inorganic gels, aqueous emulsions, liquid sugars, waxes, petroleum jelly, and/or other oils and polymeric materials.

The terms "composition" and "pharmaceutical composition" as used herein are equivalent terms referring to a composition of matter for pharmaceutical use.

The term "component" as used herein refers an ingredient that is combined with additional components/ingredients to obtain a composition.

The term "concussion" as used herein refers to a type of traumatic brain injury that is caused by a direct or indirect mechanism, for example a direct blow to the head, face or neck or a blow elsewhere on the body with an "impulsive" force transmitted to the head. The injury to the human body commonly known as a "concussion" is also referred to by various other names, such as mild traumatic brain injury (MTBI), mild head injury, mild head trauma, and mild brain injury. The relevant medical literature has used the terms concussion and MTBI interchangeably in the past, but has recently begun to favor MTBI.

A concussion is characterized by an immediate and transient alteration in brain function, including alteration of mental status and level of consciousness. Diagnosis of concussion includes one or more of the following clinical domains. Symptoms include (a) somatic (e.g., headache), cognitive (e.g., feeling like in a fog, dullness) and/or emotional symptoms (e.g., lability, depression) (b) physical signs (e.g., loss of consciousness, amnesia, convulsions), (c) behavioural changes (e.g., irritability), (d) cognitive impairment (e.g., slowed reaction times), (e) sleep disturbance (e.g., drowsiness). Sequelae of concussion include recurrent concussion, migraine headaches, depression, Parkinson's disease, Alzheimer's disease, attention deficit hyperactivity disorder, learning disability, sleep disorders, neurotransmitter production disturbance (e.g., dopamine, serotonin, acetylcholine, GABA).

The term "effective amount" as used herein means an amount sufficient to achieve the desired result and accordingly will depend on the ingredient and its desired result. Nonetheless, once the desired effect is known, determining the effective amount is within the skill of a person skilled in the art. For example, as used herein an "effective amount of the composition" is optionally the amount of composition that is sufficient to treat a subject who has suffered a traumatic brain injury.

As used herein, "opipramol" includes opipramol or a metabolite thereof, prodrugs of opipramol or a metabolite thereof. Metabolites of opipramol useful according to the methods of this invention are metabolites that have substantially the same activity or better as opipramol in alleviating symptom. A prodrug of opipramol is a derivative of opipramol that is metabolized in vivo into the active agent. Prodrugs useful according to this invention are those that have substantially the same activity or better than opipramol in treating or preventing the symptoms of trauma and stress related disorders. Methods for making prodrugs are readily known in the art (e.g., Balant, L. P., Prodrugs for the Improvement of Drug Absorption Via Different Routes of Administration, Eur. J. Drug Metab. Pharmacokinet. 15:143-153 (1990); and Bundgaard, H., Novel Chemical Approaches in Prodrug Design, Drugs of the Future 16:443-458 (1991); incorporated by reference herein).

The terms "penetration enhancement" or "permeation enhancement" as used herein refer to an increase in the permeability of skin to a pharmacologically active agent, i.e., so as to increase the rate at which the active agent permeates through the skin and enters the bloodstream. The enhanced permeation effected through the use of skin permeation enhancers, for example, through the use of a composition disclosed herein, can be observed by e.g., measuring the rate of diffusion of drug ex vivo, i.e., through animal or human skin using a diffusion cell apparatus, or in vivo, as described in the examples herein.

The terms "pharmaceutically acceptable" or "pharmacologically acceptable" refer to molecular entities and compositions that do not produce an adverse, allergic or other untoward reaction when administered to an animal, or to a human, as appropriate. The term "pharmaceutically acceptable carrier" includes any and all solvents, dispersion media, coatings, antibacterial and antifungal agents, isotonic and ab sorption delaying agents and the like. The use of such media and agents with pharmaceutical active agents is well known in the art. In some embodiments, supplementary active ingredients can also be incorporated into the compositions.

As used herein, the terms "prevention" and "preventing," when referring to a trauma and stressor-related disorder or symptom, refers to a reduction in the risk or likelihood that a mammalian subject will develop the disorder, symptom, condition, or indicator after treatment according to the invention, or a reduction in the risk or likelihood that a mammalian subject will exhibit a recurrence of the disorder, symptom, condition, or indicator once a subject has been treated according to the invention and cured or restored to a normal state (e.g., placed in remission from a targeted disorder). As used herein, the terms "treatment" or "treating," when referring to disorders, refers to inhibiting or reducing the progression, nature, or severity of the subject condition or delaying the onset of the condition.

The term "prodrug", as used herein typically refers to a derivative of an active compound or drug that requires a transformation under the conditions of use, such as within the body, to release the active drug. Prodrugs are frequently, but not necessarily, pharmacologically inactive until converted into the active drug. Prodrugs are typically obtained by masking a functional group in the drug believed to be in part required for activity with a progroup to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. A wide variety of progroups, as well as the resultant promoieties, suitable for masking functional groups in active drugs, e.g., opipramol, to yield prodrugs, are useful targets. For example, a hydroxyl functional group can be masked as a sulfonate, ester or carbonate promoiety, which can be hydrolyzed in vivo to revert the hydroxyl group. An amino functional group can be masked as an amide, carbamate, imine, urea, phosphenyl, phosphoryl or sulfenyl promoiety, which can be hydrolyzed in vivo to revert the amino group. A carboxyl group can be masked as an ester (e.g., silyl esters and thioesters), amide or hydrazide promoiety, which can be hydrolyzed in vivo to revert the carboxyl group. Other examples of suitable progroups and their respective promoieties will be apparent to those of skill in the art.

The terms "subject", "individual," or "patient," are used interchangeably herein and include any mammal, including animals, for example, primates, for example, humans, and other animals, for example, dogs, cats, swine, cattle, sheep, rodents, and horses. The compositions disclosed herein can be administered to a mammal, such as a human, but can also be other mammals, for example, an animal in need of veterinary treatment, for example, domestic animals (for example, dogs, cats, and the like), zoo and wild animals, farm animals (for example, cows, sheep, pigs, horses, and the like) and laboratory animals (for example, rats, mice, guinea pigs, and the like).

As used herein, the term "sustained release vehicle, matrix, binder, or coating material" refers to any vehicle, matrix, binder, or coating material that effectively, significantly delays dissolution of the active compound in vitro, and/or delays, modifies, or extends delivery of the active compound into the blood stream (or other in vivo target site of activity) of a subject following administration (e.g., oral administration), in comparison to dissolution and/or delivery provided by an "immediate release" formulation, as described herein, of the same dosage amount of the active compound. Accordingly, the term "sustained release vehicle, matrix, binder, or coating material" as used herein is intended to include all such vehicles, matrices, binders and coating materials known in the art as "sustained release", "delayed release", "slow release", "extended release", "controlled release", "modified release", and "pulsatile release" vehicles, matrices, binders and coatings. As used herein, "sustained release" and "sustained delivery" are evinced by a sustained, delayed, extended, or modified, in vitro or in vivo dissolution rate, in vivo release and/or delivery rate, and/or in vivo pharmacokinetic value(s) or profile.

As used herein, a "therapeutically effective amount" of opipramol for the purposes of this invention refers to the amount of the compound that prevents or alleviates or eliminates or interferes with one of the symptoms associated with a trauma or stress related disorder. A physician can readily determine when symptoms are prevented or alleviated or eliminated, for example through clinical observation of a subject, or through reporting of symptoms by the subject during the course of treatment. One skilled in the art can readily determine an effective amount of opipramol to be administered, by taking into account factors such as the size, weight, age and sex of the subject, the extent of disease penetration or persistence and severity of symptoms, and the route of administration. In the case of therapeutic agents, these terms most often refer to a measurable, statistically significant reduction in an occurrence, frequency, or severity of one or more symptom(s) of a specified trauma and stressor-related disorder, including any combination of neurological and/or psychological symptoms, diseases, or conditions, associated with or caused by the targeted disorder.

The term "transdermal" refers generally to passage of an agent across the skin layers. For example, the term "transdermal" may refer to delivery of an agent (e.g., a vaccine or a drug) through the skin to the local tissue or systemic circulatory system without substantial cutting or penetration of the skin, such as cutting with a surgical knife or piercing the skin with a hypodermic needle. The term "transdermal delivery" refers to drug delivery across the skin, usually accomplished without breaking the skin. Transdermal delivery includes delivery via passive diffusion.

The term "traumatic brain injury" as used herein refers to an injury that occurs when an external mechanical force causes damage to the brain. The force may be internal or external. For example, a traumatic brain injury can result when the head suddenly and violently hits an object, or when an object pierces the skull and enters brain tissue. Symptoms of a traumatic brain injury can be mild, moderate, or severe, depending on the extent of the damage to the brain.

The terms "treating" or "treatment" as used herein, and as are well understood in the art, mean an approach for obtaining beneficial or desired results, including clinical results. Beneficial or desired clinical results can include, but are not limited to, alleviation or amelioration of one or more symptoms or conditions, diminishment of extent of injury or disease, stabilizing (i.e. not worsening) the state of injury or disease, delaying or slowing of injury or disease progression, amelioration or palliation of the injury or disease state, diminishment of the reoccurrence of injury or disease, and remission (whether partial or total), whether detectable or undetectable. Treatment methods optionally comprise administering to a subject a therapeutically effective amount of a composition and optionally consists of a single administration, or alternatively comprise a series of applications. The length of the treatment period depends on a variety of factors, such as the severity of the condition, the age of the patient, the concentration of the composition and components of the composition, the activity of the compositions and components of the composition, and/or a combination thereof. It will also be appreciated that the effective dosage of the composition and components of the composition used for the treatment or prophylaxis may increase or decrease over the course of a particular treatment or prophylaxis regime. Changes in dosage may result and become apparent by standard diagnostic assays known in the art. In some instances, chronic administration may be required. For example, the compositions may be administered to the subject in an amount and for a duration sufficient to treat the patient.

DESCRIPTION

The present invention relates to compositions and methods for preventing, ameliorating, or alleviating neuropsychiatric symptoms and psychiatric disorders associated with TBI and related disorders consisting of administering a matrix-type transdermal patch with a composition consisting of opipramol, excluding any other component such as a pharmaceutical carrier or excipient.

A method for preventing, ameliorating or alleviating neuropsychiatric symptoms and psychiatric disorders associated with traumatic brain injuries (TBI) and related disorder consisting of administering to a human in need of such treatment by a matrix-type transdermal patch with a composition consisting opipramol in an amount effective to prevent, ameliorate or alleviate one or more symptoms of the traumatic brain injuries (TBI) related disorder, wherein the opipramol is administered in a symptom reducing effective dosage of ranges: from 5-500 mg per day, from 25 to 450 mg per day, from 40 to 450 mg per day, from 50 to 400 mg per day, from 50 to 300 mg per day, from 100 to 300 mg per day, from 150 to 300 mg per day, wherein the transdermal patch results in a 20-50% bioavailability increase, a 50%-100% increase, up to a three-fold, or greater increase, and a five-fold or greater increase in bioavailability compared to that obtained with an equivalent oral dosage form, and wherein the disorder is selected from the group consisting of traumatic brain injury (TBI), concussion, sport-related concussion, post-concussion syndrome, open head injury, closed head injury, contusion, diffuse axonal injury, coup-contre coup injury, second impact syndrome, penetrating injury, shaken baby syndrome, locked in syndrome, anoxic brain injury, hypoxic brain injury and Alzheimer's disease, Parkinson's disease, Huntington's disease, and ALS, wherein the method further consisting coordinately administering (a) one or more additional therapeutic agent in an amount effective to prevent, ameliorate or alleviate one or more symptoms of the disorder, (b) coordinately administering one or more non-pharmacological treatments effective to prevent, ameliorate or alleviate one or more symptoms of the disorder, or (c) both, and the one or more additional therapeutic agent is selected from the group consisting of anti-depressant, mood-stabilizing, anxiolytic, anticonvulsant, stimulant, antipsychotic, antiaddictive, appetite suppressant drugs and opiate agonists.

Traumatic brain injuries (TBI) and related disorders are frequently accompanied by acute stress reactions (ASR), insomnia and other neuropsychiatric symptoms (cognitive dysfunction, anxiety, irritability, depression), and have been associated with the development of subsequent PTSD. Studies have also found elevated rates of PTSD and other psychological sequelae in military TBI compared to civilian TBI. Acute stress reactions and other neuropsychiatric symptoms may be important mediators of post concussive severity and presence or persistence of these symptoms may severely impair return to duty functioning. (MacDonald, Brain 2015) (Norris, J N Brain Injury 2014). Currently there are no FDA approved medication-based therapies for the treatment of psychiatric or cognitive symptoms in TBI, nor are there approved therapies for acute stress reactions or acute stress disorder.

Acute post-concussive syndrome following TBI involves a complex of psychiatric and cognitive symptoms including the affective spectrum (depression in particular), anxiety symptoms, irritability, dissociation experiences (emotional numbness, trouble remembering, feelings of "unreality" or living in a "dream state"), as well as other PTSD like symptoms. These may be complexed with somatic symptoms, cognitive dysfunction, and, frequently, insomnia.

The disclosure includes methods for treating a traumatic brain injury comprising administering an effective amount of the compositions described herein to a subject in need thereof. The disclosure also includes the use of the compositions described here for treating a subject who has suffered a traumatic brain injury.

In one embodiment, the traumatic brain injury is a concussion. Accordingly, the disclosure also relates to methods for treating a concussion comprising administering an effective amount of the compositions described herein to a subject in need thereof. The disclosure also relates to the use of the compositions described here for treating a subject who has suffered a concussion.

In one embodiment, the present methods are used for treating a subject who has at least 1, 2, 3, 4 or 5 concussion symptoms. Concussion symptoms include, but are not limited to, headache, pressure in head, neck pain, nausea or vomiting, dizziness, blurred vision, sensitivity to light, sensitivity to noise, feeling slowed down, feeling "in a fog", "not feeling right", difficulty concentrating, difficulty remembering, fatigue or low energy, confusion, drowsiness, trouble falling asleep, increased emotions, irritability sadness and nervousness or anxiety. Optionally, the present methods are used for treating a subject who has been diagnosed with a traumatic brain injury or a concussion.

In another embodiment, the present methods are used for treating a post-concussive syndrome. Post-concussive syndromes include, but are not limited to, post-concussion disease, prolonged post-concussion disease, mild cognitive impairment, chronic traumatic encephalopathy and dementia pugilistica. In further embodiments the present methods are used for treating long-term complications of concussion such as Alzheimers disease, Parkinsons disease, amyotrophic lateral sclerosis (ALS) or post concussive depression.

In an embodiment, the composition is administered once a day to a subject in need thereof. In another embodiment, the composition is administered every other day, every third day or once a week. In another embodiment, the composition is administered twice a day. In still another embodiment, the composition is administered three times a day or four times a day. In a further embodiment, the composition is administered at least once a day for at least 1, 2, 3, 4, 5, 6, 7, 8, 9, 10, 11 or 12 weeks. In still a further embodiment, the composition is administered at least once a day for a longer term such as at least 4, 6, 8, 10, 12 or 24 months. Administration in one embodiment includes but is not limited to a dosage of 10 ng-50 mg of composition at a frequency of minimum 1, 2, 3 or 4 times or more per day. Optionally, administration continues until all symptoms are resolved and cleared by medical personnel via standardized testing such as SCAT 2.

In one embodiment, the composition is administered within 1, 2, 3, 5 or 7 days of the traumatic brain injury. In other embodiments, the composition is administered within 1, 2, 3, 5 or 7 days of the appearance of symptoms of a traumatic brain injury.

In one embodiment, the composition is administered at least once a day until the condition has ameliorated to where further treatment is not necessary. In another embodiment, the composition is administered until all symptoms of the traumatic brain injury are resolved. In another embodiment, the composition is administered until the subject is able to return to physical activity or "cleared to play" in a particular sport. In an even further embodiment, the composition is administered for at least 1, 2, 3, 6, 8, or 12 or 24 months after the subject is asymptomatic.

The compositions of the present disclosure are useful and effective when administered to treat a traumatic brain injury such as a concussion. The amount of each component present in the composition will be the amount that is therapeutically effective, i.e., an amount that will result in the effective treatment of the condition (e.g., traumatic brain injury) when administered. The therapeutically effective amount will vary depending on the subject and the severity and nature of the injury and can be determined routinely by one of ordinary skill in the art.

It will also be appreciated that the effective dosage of the composition and the individual components of the composition for the treatment may increase or decrease over the course of a particular treatment regime. In some instances, chronic administration may be required.

In some embodiments, the composition is formulated for administration to a subject such as a human. In particular embodiments, the composition is formulated for oral administration. Optionally, the composition is formulated for inhalative, rectal or parenteral administration, including dermal, intradermal, intragastral, intracutaneous, intravasal, intravenous, intramuscular, intraperitoneal, intranasal, intravaginal, intrabuccal, percutaneous, subcutaneous, sublingual, topical or transdermal administration.

The compositions for oral administration optionally include, but are not limited to, solid, semi-solid, gel, paste, liquid, crystalline or encapsulated forms. Non-limiting examples of these forms include capsules, tablets, suspensions, powders, suspended-release formulations, solutions, emulsions and syrups. In further embodiments, the composition is used as an inhalant or suppository. In one embodiment, the compositions for oral administration range from 5 to 50,000 mg, optionally 10 to 1000 mg or 15 to 250 mg.

In some embodiments, the composition is formulated such that a single dose is contained in one capsule or tablet or gel pack. In other embodiments, the composition is formulated such that a single dose is contained in at least 2, 3, 4 or more individual capsules, tablets, packet, or packets.

In other embodiments, the composition includes a pharmaceutically acceptable carrier, excipient, buffer or stabilizer. Suitable pharmaceutically acceptable carriers include essentially chemically inert and nontoxic materials that do not interfere with the effectiveness of the biological activity of the pharmaceutical composition. Suitable vehicles are described, for example, in Remington's Pharmaceutical Sciences (Remington's Pharmaceutical Sciences, 20th ed., Mack Publishing Company, Easton, Pa., USA, 2000). Examples of suitable pharmaceutical carriers include, but are not limited to, water, saline solutions, glycerol solutions, ethanol, N-(1(2,3-dioleyloxy)propyl)N,N,N-trimethylammonium chloride (DOTMA), diolesylphosphotidyl-ethanolamine (DOPE), and liposomes. Such compositions contain a therapeutically effective amount of the components in the composition, together with a suitable amount of carrier so as to provide the form for direct administration to the patient.

The composition may also include flavor and/or color additives. For example, beet powder may be added for flavor.

In one or more embodiments, the opipramol composition is administered in a single dose. In some embodiments, the opipramol composition is administered at a dosage from 10 ng/kg per day to 10 mg/kg per day. In some embodiments, the opipramol composition is administered at a dosage of 0.2-200 mg/kg per day. In some embodiments, the opipramol composition is administered at a dosage of 2-100 mg/kg per day. In one preferred embodiment, an opipramol composition is administered passively such as by sublingual, inner ear or pulmonary delivery.

In one or more embodiments, the opipramol composition is administered at a symptom reducing effective dosage of from about 50 to about 300 mg per day when dosed orally.

In one or more embodiments, the opipramol composition is administered at a symptom reducing effective dosage of from about 0.001 to about 10 mg/kg per day when dosed intravenously or from about 0.01 to about 100 mg/kg when dosed p.o. in either an adult or child. The abbreviation "p.o." herein refers to per os or "by mouth" as a route for administration of medications.

In one or more embodiments, the opipramol composition is administered at a symptom reducing effective dosage of from about 0.005 to about 1 mg/kg per day when dosed intravenously or from about 0.1 to about 10 mg/kg when dosed p.o. in either an adult or child.

In one or more embodiments, the opipramol composition is administered at a dosage as low as 0.005 mg/kg i.v. and 0.01 mg·kg p.o. The upper limit of the dosage range is about 10 mg/kg i.v. and 100 mg/kg p.o.

The pharmaceutical composition may be in unit dosage form, e.g., as tablets or capsules. In such form, the composition is sub-divided in unit doses containing appropriate quantities of the active ingredient; the unit dosage forms can be packaged compositions, for example, packeted powders or vials or ampoules. The unit dosage form can be a capsule, cachet or tablet itself, or it can be the appropriate number of any of these in package form. The quantity of the active ingredient in a unit dose of composition may be varied or adjusted from 5 to 500 mg per day, from 25 to 450 mg per day, from 25 to 400 mg per day, from 50 to 400 mg per day, from 50 to 300 mg per day, from 100 to 300 mg per day, from 200 to 300 mg per day, according to the particular need and the activity of the active ingredient. The usual oral recommended dose of opipramol for humans may be from 5 to 500 mg per day, from 25 to 450 mg per day, from 25 to 400 mg per day, from 50 to 400 mg per day, from 50 to 300 mg per day, from 100 to 300 mg per day, from 200 to 300 mg per day and this dose may be administered in two or three divided doses. A maximum recommended daily dose for humans would be about 500 mg, 450 mg, 400 mg, 350 mg, 300 mg, or less but it will be understood by one skilled in the art that dosage under this invention will be determined by the particular circumstances surrounding each case. Higher or lower doses are also contemplated.

Also contemplated within the present disclosure is the use of compositions described herein as a preventive or prophylactic measure against a traumatic brain injury such as concussion. In some embodiments, the compositions are administered to a subject prior to a traumatic brain injury. The disclosure also includes methods for treating subjects who are at risk of a traumatic brain injury or who have previously suffered from a traumatic brain injury comprising administering to the subjects an effective amount of the compositions described herein. In other embodiments, the compositions are used for treating a subject who is suspected of having a traumatic brain injury or a subject who may have suffered from a traumatic brain injury. The subject may or may not display symptoms of a traumatic brain injury.

In one embodiment opipramol therapy can be carried out indefinitely to alleviate the symptoms of interest and frequency of dosage may be changed to be taken as needed. The period of treatment should be carried out for as long as necessary to alleviate one or more of the core symptoms of each of the trauma and stress related disorders mentioned.

In another embodiment of the invention, opipramol is administered in combination with a drug which may further alleviate the symptoms of the traumatic brain injury (TBI) or related disorders. The drugs may be administered sequentially or concurrently with the opipramol.

In another aspect, the invention may be employed for treating or preventing the development (either the initiation, consolidation or perpetuation) of a traumatic brain injury (TBI) or related disorders following a trauma-inducing event, including concussion, sport-related concussion, and post-concussion syndrome.

In another aspect, the invention may be employed for treating or preventing the development (either the initiation, consolidation or perpetuation) of a traumatic brain injury (TBI) or related disorders following a trauma-inducing event, including open head injury, closed head injury, concussion, contusion, diffuse axonal injury, coup-contre coup injury, second impact syndrome, penetrating injury, shaken baby syndrome, locked in syndrome, anoxic brain injury and hypoxic brain injury.

In another aspect, the invention may be employed for treating or preventing the development (either the initiation, consolidation or perpetuation) of a traumatic brain injury (TBI) or related disorders following a trauma-inducing event, including neurodegenerative disorder involving inflammation of the brain such as Alzheimer's disease, Parkinson's disease, Huntington's disease, and ALS.

The present invention provides novel methods and combined drug compositions, dosage forms, packages, and kits for the treatment or prevention of symptoms associated with traumatic brain injury (TBI) or related disorders.

The methods and compositions of the invention use of opipramol alone or in combination with other therapeutic agents or treatments to modulate, prevent, alleviate, ameliorate, reduce or treat the symptoms of traumatic brain injury (TBI) and related disorders. In some embodiments, administration of the compositions and methods of the present invention may prevent a traumatic brain injury (TBI) or related disorder from developing. In other embodiments, administration of the compositions and methods of the present invention may prevent recurrent episodes of a traumatic brain injury (TBI) or related disorder.

Subjects amenable to treatment according to the invention include mammalian subjects, including humans, suffering from or at risk for any of a variety of disorders including traumatic brain injury (TBI), concussion, sport-related concussion, post-concussion syndrome, open head injury, closed head injury, contusion, diffuse axonal injury, coup-contre coup injury, second impact syndrome, penetrating injury, shaken baby syndrome, locked in syndrome, anoxic brain injury, hypoxic brain injury and neurodegenerative disorders involving inflammation of the brain such as Alzheimer's disease, Parkinson's disease, Huntington's disease, and ALS.

Within the methods of the invention, opipramol is administered in an amount effective to treat a specified disorder alone or in combination with one or more additional therapeutic treatments or drugs including, but not limited to, drugs from the general classes of anti-depressant, mood-stabilizing, anxiolytic, anticonvulsant, antipsychotic, antiaddictive, appetite suppressant drugs and opiate agonists. (See, e.g., R J. Baldessarini in Goodman & Gilman's The Pharmacological Basis of Therapeutics, 9th Edition, Chapter 18, McGraw-Hill, 1996 for a review).

In one or more embodiments, the additional treatments include short wave light therapy, exposure therapy, psychotherapy, physical and cognitive rest, acceptance and commitment therapy, vestibulo-ocular therapy, pulsed magnetic fields, electroconvulsive therapy (ECT), Cogsmart Therapy, SPECT neuroimaging, neuropsychological assessment, transcranial magnetic stimulation, interpersonal and cognitive/behavioral therapies, light therapies and one or more additional agent.

In one or more embodiments, the formulations use an opipramol such as opipramol dihydrochloride alone or in combination with one or more therapeutic drugs including, but not limited to, amantadine, prazosin, propranolol, Alprazolam, Ambien, Ambien CR, amitriptyline, Amphetamine, Amytal Sodium (amobarbital sodium), Amytriptiline, aripiprazole, asenapine, atorvastatin, brexipiprazole, Bromocriptine, bupropion, buspirone, Butisol (butabarbital sodium), Carbamazepine (Tegretol), Carbidopa, Chlorpromazine, ciclosporin A, Citalopram, Clonazepam, clonidine, Dalmane (flurazepam), desipramine, Desvenlafaxine, dextroamphetamine, donepezil, Doral (quazepam), duloxetine, escitalopram (Lexapro), fluoxetine, fluphenazine, fluvoxamine (Luvox), gabapentin, Galantamine, gepirone, Halcion (triazolam), Haloperidol, iloperidone, Imidazopyridines, imipramine (Tofranil), Intermezzo (zolpidem), isocarboxazid (Marplan), Lamotrigine (Lamictal), Levodopa, levomilnacipran, Lisdexamfetamine Dimesylate, Lodosyn (carbidopa-levodopa), Lorazepam, Lunesta (eszopiclone), lurasidone, Mebaral (mephobarbital), melatonin receptor stimulator, memantine, Methylphenidate, Mirapex (pramipexole), Mirtazapine, moclobemide, nefazodone, Nembutal (phenobarbital), nortriptyline, Notec (chloral hydrate), Nuvigil (armodafinil), olanzapine, omega-3 fatty acids, Oxcarbazepine (Trileptal), paliperidone, Parlodel (bromocriptine mesylate), Paroxetine, Permax (pergolide mesylate), perphenazine (Triavil), phenelzine (Nardil), Pindolol, Precedex (dexmedetomidine hydrochloride), pregabalin, progesterone, Prosom (estazolam), protriptyline, Provigil (modafinil), pyritinol, quetiapine, rasagiline (Azilect), Requip, Requip XL (ropinirole Hcl), Restoril (temazepam), risperidone, Rivastigmine, Rozerem (ramelteon), Seconal Sodium Pulvules (secobarbital sodium), selegiline (Eldepryl, Zelapar), sertraline, simvastatin, Sinemet, Sinemet CR, sodium valproate (Depacon, Epilim), Sonata (pyrazolopyrimidine), Suvorexant (Belsomra), topiramate, transexamic acid, tranylcypromine (Parnate), trazodone, trimipramine (Surmontil), Valium (diazepam), valproate semisodium (Depakote), Valproic acid (Depakine), Venlafaxine, vilazodone (Viibryd), vortioxetine (Trintellix), Xyrem (sodium oxybate) and ziprasidone.

Exemplary formulations use an opipramol such as opipramol dihydrochloride alone or in combination with one or more psychotherapeutic drugs including, but not limited to, anti-depressants, mood-stabilizing, anxiolytic, anticonvulsant, antipsychotic, antiaddictive, appetite suppressant drugs and opiate agonists.

Dosing and therapeutic benefits of the opipramol coordinately administered with the one or more additional therapeutic drug will typically have similarly favorable therapeutic effects and comparable side effects as a therapeutic benefit and side effect profile achieved in control patients treated with the psychotherapeutic agent alone. However, in certain embodiments the dosage of the psychotherapeutic agent may be lowered and yet in combination with the opipramol, will still have comparable therapeutic benefits and similar side effects as a therapeutic benefit and side effect profile achieved in control patients treated with a higher dosage of the psychotherapeutic agent alone. Additionally, the opipramol, may also be present in lower or sub-therapeutic amounts yet in combination with the psychotherapeutic drug will still have comparable therapeutic benefits and similar side effects as a therapeutic benefit and side effect profile achieved in control patients treated with a higher dosage of the opipramol alone.

Within more detailed embodiments of the invention, the compositions and methods of the invention achieve substantial therapeutic benefit in terms of a clinical reduction in incidence, development, rate, recurrence, or severity of disorders including traumatic brain injury (TBI) or related disorder. In related embodiments, the compositions and methods of the invention measurably alleviate or prevent one or more symptoms of the traumatic brain injury (TBI) or related disorder.

Transdermal administration of opipramol or the coordinate treatment method or combinatorial drug composition of the invention to suitable subjects (e.g., qualified subjects suffering from a trauma and stressor-related disorder or at increased risk for developing a trauma and stressor-related disorder) will yield a reduction in one or more target symptom(s) associated with the selected anxiety disorder or development of the anxiety disorder by at least 10%, 20%, 30%, 50% or greater, up to a 75-90%, or 95% or greater, compared to placebo-treated or other suitable control subjects. Comparable levels of efficacy are contemplated for the entire range of trauma and stressor-related disorder described herein, including all contemplated neurological and psychiatric disorders, and related conditions and symptoms, for treatment or prevention using the compositions and methods of the invention. These values for efficacy may be determined by comparing accepted therapeutic indices or clinical values for particular test and control individuals over a course of treatment/study, or more typically by comparing accepted therapeutic indices or clinical values between test and control groups of individuals using standard human clinical trial design and implementation.

Therapeutic efficacy can alternatively be demonstrated by a decrease in the frequency or severity of symptoms associated with the treated condition or disorder, or by altering the nature, occurrence, recurrence, or duration of symptoms associated with the treated condition or disorder. Therapeutic efficacy with the treated condition or disorder, or by altering the nature, recurrence, or duration of symptoms associated with the treated condition or disorder. In this context, "effective amounts," "therapeutic amounts," "therapeutically effective amounts," and "effective doses" of psychotherapeutic drugs and opipramols within the invention can be readily determined by ordinarily skilled artisans following the teachings of this disclosure and employing tools and methods generally known in the art, often based on routine clinical or patient-specific factors. In some embodiments, therapeutic efficacy will be determined prophylactically in that fewer or no subjects will develop the traumatic brain injury (TBI) or related disorder in comparison to the related population.

Efficacy of the coordinate treatment methods and drug compositions of the invention will often be determined by use of conventional patient surveys or clinical scales to measure clinical indices of traumatic brain injury (TBI) or related disorder in subjects. The methods and compositions of the invention will yield a reduction in one or more scores or selected values generated from such surveys or scales completed by test subjects by at least 10%, 20%, 30%, 50% or greater, up to a 75-90%, or 95% compared to correlative scores or values observed for control subjects treated with placebo or other suitable control treatment. In at risk populations, the methods and compositions of the invention will yield a stable or minimally variable change in one or more scores or selected values generated from such surveys or scales completed by test subjects. More detailed data regarding efficacy of the methods and compositions of the invention can be determined using alternative clinical trial designs.

In addition to opipramol, compositions of the present invention may include prodrugs of opipramol, which are metabolized or converted to yield active opipramol. Prodrugs and other modified forms of opipramol may be employed to increase its solubility and commensurately, its oral bioavailability. Increasing the bioavailability of opipramol may result in reduced inter-subject variability in drug exposure and a more normalized therapeutic delivery and effectiveness.

Prodrugs include compounds of the invention, for example opipramol or opipramol derivatives, wherein one or more appropriate active groups or chemically modifiable moieties of the parent drug have been modified to improve solubility (in physiological solutions, including blood and other tissues and compartments of mammalian subjects), bioavailability, half-life, and/or pharmacological activity in vivo, and generally the subject modification may be reversed upon administration to a mammalian, e.g., human, subject. Reversion is usually achieved by an enzyme naturally present in the subject, such as an endogenous phosphatase, though it is possible for a second agent to be administered together with a prodrug in order to mediate the prodrug reversion to a more active form, most often the parental drug form, in vivo.

Within the methods and compositions of the invention, the solubility, bioavailability, half-life, and/or pharmacological activity in vivo of opipramol can be increased using novel opipramol prodrug derivatives, including but not limited to phosphoester prodrugs of opipramol. In one or more embodiments, the prodrug modifications useful within the invention for opipramol include ester modifications, the parent drug is modified to an ester derivative prodrug form, and reversion may be carried out by an esterase, etc.

Additional prodrug ester derivatives of opipramol and other active compounds for use within the invention are provided herein, which may be produced by additional prodrug ester modifications directed to, for example, the following alternative active groups or moieties of the subject parent compound, alkyl, aryl, arylalkyl, alkoxy, alkoxyl, etc., modified to any of a range of contemplated ester prodrug forms convertible in vivo by reversion to the parent compound, or otherwise converted to yield a modified, active drug compound in vivo. In accordance with this aspect of the invention, additional convertible ester prodrug derivatives of opipramol and other therapeutic compounds for use within the invention will include a range of physiologically hydrolyzable esters, including alkylbenzyl, methoxybenzyl, indanyl, phthalyl, methoxymethyl, alkanoyloxy-alkyl, acetoxymethyl, alkoxycarbonyloxy-alkyl, glycyloxymethyl, phenylglycyloxymethyl, and other physiologically hydrolyzable esters that may be prepared using conventional techniques known in the art.

Useful methods and materials to produce additional prodrug derivatives of opipramol and other therapeutic compounds for use within the invention may be found, for example in Design of Prodrugs, edited by H. Bundgaard, (Elsevier, 1985) and Methods in Enzymology, 112:309-396, edited by K. Widder, et al. (Academic Press, 1985); A Textbook of Drug Design and Development, edited by Krosgaard-Larsen and H. Bundgaard, Chapter 5, "Design and Application of Prodrugs," by H. Bundgaard, pp. 113-191 (1991); and H. Bundgaard, Advanced Drug Delivery Reviews, 8:1-38 (1992), each incorporated herein by reference.

The solubility, bioavailability and/or pharmacological activity of opipramol can also be increased by modifying the compound to yield salt and other forms of opipramol that have an increased solubility compared to the parent compound. Such modifications include modification with an acid ester. Pharmaceutically acceptable salts of opipramol or other active therapeutic compounds for use within the methods and compositions of the invention include salts formed with inorganic and organic bases. Such salts, including ammonium salts; alkali metal salts, such as lithium, sodium and potassium salts; alkaline earth metal salts, such as calcium and magnesium salts; salts with organic bases, such as amine like salts (e.g., dicyclohexylamine salt, benzathine, N-methyl-D-glucamine, and hydrabamine salts); and salts with amino acids like arginine, lysine and the like; and zwitterions, the so-called "inner salts". Pharmaceutically acceptable salts in this context also include acid addition salts, for example salts formed with strong inorganic acids, such as mineral acids, for example sulfuric acid, phosphoric acid or a hydrohalic acid such as HCl or HBr; with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as (C1-4)alkyl or arylsulfonic acids which are unsubstituted or substituted, for example by halogen, for example methanesulfonic acid or p-toluenesulfonic acid.

Prodrug modifications, formation of pharmaceutically acceptable salts, and other modifications of opipramol and other therapeutic compounds described herein yield improved solubility, bioavailability, and/or pharmacological efficacy, e.g., of opipramol, of at least 10%, 20%, 20-30%, up to 30-50%, 50-70%, 100%, 200%, or greater, e.g., as compared to an equivalent dose of the unmodified parent drug, such as opipramol. The improved solubility, bioavailability, and/or pharmacological efficacy of opipramol prodrugs and salts and other modified therapeutic compounds within the invention can be readily determined using standard dissolution assays, pharmacokinetic studies, and/or in vitro and in vivo models of pharmacological activities, including in more detailed aspects known useful physiological models of trauma and stressor-related disorder, such as ASD and PTSD. The increase in bioavailability and/or pharmacological activity of ester and other opipramol prodrugs, opipramol salts, and other modified therapeutic compounds provided herein, as determined e.g., using physiological models, such as animal models and/or human clinical studies, will be at least 10%, 20%, or 20-30%, up to 30-50%, 50-70%, 100%, 200% or greater compared to an equal dose of unmodified opipramol parent drug.

Compositions of the invention may include opipramol or a combination opipramol and one or more psychotherapeutic agents. In one or more embodiments of the invention, opipramol is administered in combination with a drug, which may further alleviate the symptoms of the traumatic brain injury (TBI) or related disorder. The drugs may be administered sequentially or concurrently with the opipramol. The drugs include an alpha-1-adrenergic receptor antagonist, a beta-adrenergic antagonist, an anticonvulsant, antipsychotic drug, a benzodiazepine, a glucocorticoid, a glucocorticosteroid, a sertonin 1A receptor active drug, a tricyclic or heterocyclic antidepressant drug, a selective serotonin reuptake inhibitor or a serotonin-norepinephrine reuptake inhibitor.

In a further aspect, the invention is a pharmaceutical composition. The pharmaceutical composition comprises a therapeutically effective amount of opipramol in combination with a drug selected from the group consisting of an alpha-1-adrenergic receptor antagonist, a beta-adrenergic antagonist, an anticonvulsant, antipsychotic drug, a benzodiazepine, a glucocorticoid, a glucocorticosteroid, a sertonin 1A receptor active drug, a tricyclic or heterocyclic antidepressant drug, a selective serotonin reuptake inhibitor or a serotonin-norepinephrine reuptake inhibitor.

In certain embodiments of the invention, an adjunctive psychotherapeutic agent is employed in combination with the opipramol. The psychotherapeutic agent may be selected from known anti-depressant drugs, for example, any species within the broad families of tri-cyclic anti-depressants (TCAs) including, but not limited to, amitriptyline, imipramine, or desipramine; specific monoamine reuptake inhibitors, e.g., selective serotonin reuptake inhibitors (SSRIs) including, but not limited to, fluoxetine, fluvoxamine, sertraline and paroxetine, selective norepinephrine reuptake inhibitors, selective dopamine reuptake inhibitors, multiple monoamine reuptake inhibitors, monoamine oxidase inhibitors (MAOIs), noradrenaline reuptake inhibitors (NRIs), multiple monoamine reuptake inhibitors, e.g., that inhibit both serotonin and norepinephrine reuptake (SNRIs) including, but not limited to, venlafaxine and duloxetine, and indeterminate (atypical) anti-depressants are useful within this aspect of the invention. The psychotherapeutic agent may additionally include atypical antipsychotics including, but not limited to, Aripiprazole, Ziprasidone, Risperidone, Quetiepine, or Olanzapine or anticonvulsants including but not limited to lamotrigine, carbamazepine, oxcarbazepine, valproate, levetriacetam, and topiramate.

Within certain embodiments of the invention, one or more of the anti-depressant drugs is coordinately administered or combinatorially formulated with opipramol to treat a traumatic brain injury (TBI) or related disorder. Single drugs, or multiple drugs from one or more of the indicated drug classes, may be co-administered, simultaneously or sequentially, with the opipramol, which may be combinatorially formulated with the psychotherapeutic therapeutic drug or provided in a separate dosage form.

In other detailed embodiments of combinatorial formulations and coordinate treatment methods of the invention, examples of useful anti-depressant agents include, but are not limited to, one or more of the following: MAOIs, such as phenelzine, nortriptyline, selegiline and tranylcypromine; SSRIs, such as paroxetine, fluoxetine, citalopram, trazodone, fluvozamine and sertraline; Tricyclic anti-depressants, such as amitriptyline, desipramine, clomipramine, doxepine, trimipramine, amoxapine, protripyline and imipramine; Tetracyclic anti-depressants; Norepinephrine uptake inhibitors; Selective noradrenaline reuptake inhibitors; Serotonin and norepinephrine reuptake inhibitors, such as venlafaxine and duloxetine; and other anti-depressant agents such as maprotiline, nefazodone, and bupropion. In additional detailed embodiments the combinatorial formulations and coordinate treatment methods of the invention employ one or more useful psychotherapeutic agents selected from the following: SSRI's, such as Lexapro® (escitalopram HBr; indicated to treat depression and generalized anxiety disorder Celexa® (citalopram), Prozac®, Luvox® (fluvoxamine; also indicated to treat obsessive symptoms), Zoloft® (sertraline; also indicated to treat post-traumatic stress syndrome); Tricyclics, such as Amitriptyline, Desipramine, Nortriptyline; SSNRIs, such as Cymbalta® (Duloxetine), Effexor®, and desvenlafaxine; Tetracyclics, such as Remeron® (mirtazepine); MAOIs, such as Nardil® (phenelzine), and Parnate® (tranylcypromine); Serzone® (nefazodone; a phenylpiperazine); Trazodone® (a triazolopyridine); and Wellbutrin® (bupropion; an aminoketone). In additional detailed embodiments the combinatorial formulations and coordinate treatment methods of the invention employ one or more useful psychotherapeutic agents selected from the following: Amitriptyline; Amoxapine; Aripiprazole; Atomoxetine; Bupropion; Citalopram; Clomipramine; Desipramine; Desvenlafaxine; Dothiepin; Doxepin; Duloxetine; Escitalopram; Fluoxetine; Fluvoxamine; Imipramine; Isocarboxazid; Lofepramine; Maprotiline; Milnacipran;

Mirtazapine; Moclobemide; Nefazodone; Notriptyline; Paroxetine; Phenelzine; Protriptyline; Quetiapine; Reboxetine; Selegiline; Sertraline; Tianeptine; Tranylcypromide; Trazodone; Trimipramine; and Venlafaxine.

In other detailed combinatorial formulations and coordinate treatment methods of the present invention, the psychotherapeutic agent is an anxiolytic drug agent including, but not limited to, benzodiazepines, such as alaprazolam, chlordiazepoxide, clonazepam, chl orazep ate, diazepam, lorazepam, oxazepam and prazepam; non-benzodiazepine agents, such as buspirone; and tranquilizers, such as barbituates.

Benzodiazepines, anti-depressants, selective serotonin reuptake inhibitors and the azapirone agonist of the serotonin 1A receptor, buspirone (Lydiard et al., 1996) have been used with some success in the treatment of anxiety and anxiety disorders and are therefore contemplated for effective use within the methods and compositions of the invention.

In one or more other detailed combinatorial formulations and coordinate treatment methods of the present invention, the psychotherapeutic agent is one or more steroidal anti-inflammatory agents are chosen from mineralosteroids and glucorticosteroids. In some embodiments, one or more steroidal anti-inflammatory agents are chosen from those having a pregna-1,4-diene-3,20 dione core structure. In one aspect of this embodiment, the one or more steroidal anti-inflammatory agents having a pregna-1,4-diene-3,20 dione core structure are chosen from dexamethasone, fluorometholone, betamethasone, corticosterone, and prednisolone. Examples of steroidal anti-inflammatory agents include, but are not limited to, budesonide, pregnenolone, predni sone, prednisolone, methylprednisolone, triamcinolone, dexamethasone, betamethasone, parametasone, cortisone, and hydrocortisone.

In one or more other detailed combinatorial formulations and coordinate treatment methods of the present invention, the psychotherapeutic agent is one or more glucocorticoid or glucocorticosteroid. The one or more glucocorticoids contained in a composition according to the invention is selected from the group consisting of hydrocortisone, cortisone, prednisolone, prednisone, methylprednisone, triamcinolone, paramethasone, betamethasone, dexamethasone and fludrocortisone including pharmaceutically acceptable esters, salts and complexes thereof.

Examples of the one or more glucocorticoids (as discussed above) are synthetic glucocorticoids such as, e.g., hydrocortisone 21-succinate, prednisolone, prednisone, methylprednisone, triamcinolone, paramethasone, betamethasone, dexamethasone and fludrocortisone including pharmaceutically acceptable esters, salts and complexes thereof. An especially suitable example is hydrocortisone or hydrocortisone 21-succinate or a pharmaceutically acceptable salt thereof.

As indicated in the sections above, the one or more glucocorticoids may be a mixture of glucocorticoids.

In one or more embodiments, the one or more glucocorticoid is hydrocortisone. In one or more embodiments, the hydrocortisone may be substituted for cortisone. The term "cortisone" includes "cortisone acetate".

Due to different potencies of the glucocorticoids, the term "hydrocortisone equivalents" is used. The term "hydrocortisone equivalents" is used herein to define the amount in mg of a specific glucocorticoid that corresponds to 1 mg of hydrocortisone for the purpose of systemic glucocorticoid therapy as generally understood by medical practitioners. The term is based on the fact that the individual glucocorticoids have different potencies and in order to achieve a desired therapeutic effect different doses of the individual glucocorticoids are required.

The glucocorticoids of the combination pharmaceutical composition should each include a hydrocortisone equivalent daily dose of 5-300 mg. For the purpose of comparison, a table is given herein describing the equivalent milligram dosage of the various glucocorticoids. Thus, other forms of synthetic glucocorticoids in equivalent doses might be used. Normally, a pharmaceutical composition according to the present invention contains a total amount of hydrocortisone equivalents expressed as hydrocortisone in the composition from about 1 to about 300 mg. In specific embodiments, the total amount of hydrocortisone equivalents in the composition is from about 1 to about 300 mg such as, e.g., from about 1 to about 250 mg, from about to about 200 mg, from about 5 to about 150 mg, from about 5 to about 10 mg or from about 10 to about 80 mg.

In some embodiments of the invention, dexamethasone is used in the combination treatments and co-formulations. Dexamethasone is available from a number of sources including Par Pharmaceuticals (Woodcliff Lake, N.J.). In one embodiment, dexamethasone is administered in an amount from about 0.25 mg to about mg per day. In one aspect of this embodiment, dexamethasone is administered in an amount from about 0.25 mg to about 25 mg, 0.25 mg to about 20 mg, 0.25 mg to about mg, 0.25 mg to about 10 mg, or 0.25 mg to about 5 mg per day. In one aspect of this embodiment, dexamethasone is administered in an amount from about 100 or less mg, or less mg, 80 or less mg, 70 or less mg, 60 or less mg, or 50 or less mg per day. In one aspect of this embodiment, dexamethasone is administered in an amount from about 0.5 or more mg, 5 or more mg, 10 or more mg, 20 or more mg, 30 or more mg, or more mg, or 50 or more mg per day.

In some aspects of the invention, budesonide is used in the combination treatments and co-formulations. Budesonide is available from a number of sources including Astrazeneca (Willimgtom, Del.). In one embodiment, budesonide is administered in an amount from about 0.25 mg to about 10 mg per day. In one aspect of this embodiment, budesonide is administered in an amount from about 0.25 mg to about 7.5 mg, 0.25 mg to about 6.5 mg, 0.25 mg to about 5.5 mg, 0.25 mg to about 5.0 mg, or 0.25 mg to about 4.5 mg per day. In one aspect of this embodiment, budesonide is administered in an amount from about 10 or less mg, 9 or less mg, 8 or less mg, 7 or less mg, 6 or less mg, or 5 or less mg per day. In one aspect of this embodiment, cortisone is administered in an amount from about 0.25 or more mg, 1 or more mg, 2 or more mg, 3 or more mg, 4 or more mg, or 5 or more mg per day.

In some aspects of the invention, cortisone is used in the combination treatments and co-formulations. Cortisone is available from a number of sources including Pfizer (NY, N.Y.). In one embodiment, cortisone is administered in an amount from about 10 mg to about 300 mg per day. In one aspect of this embodiment, cortisone is administered in an amount from about 10 mg to about 275 mg, 10 mg to about 250 mg, 10 mg to about 200 mg, 10 mg to about 175 mg, or 10 mg to about 150 mg per day. In one aspect of this embodiment, cortisone is administered in an amount from about 200 or less mg, 150 or less mg, 125 or less mg, 100 or less mg, 90 or less mg, or 80 or less mg per day. In one aspect of this embodiment, cortisone is administered in an amount from about 20 or more mg, 40 or more mg, 60 or more mg, or more mg, 100 or more mg, or 150 or more mg per day.

In some aspects of the invention, betamethasone is used in the combination treatments and co-formulations. Betamethasone is available from a number of sources including Schering-Plough (Kenilworth, N.J.). In one embodiment, betamethasone is administered in an amount from about 0.25 mg to about 25 mg per day. In one aspect of this embodiment, betamethasone is administered in an amount from about 0.25 to about 20 mg, 0.25 mg to about 5.5 mg, 0.25 mg to about 5.0 mg, or 0.25 mg to about 4.5 mg per day. In one aspect of this embodiment, betamethasone is administered in an amount from about 7.5 or less mg, 7 or less mg, 6.5 or less mg, 6 or less mg, 5.5 or less mg, or 5 or less mg per day. In one aspect of this embodiment, betamethasone is administered in an amount from about 0.25 or more mg, 1 or more mg, 2 or more mg, 3 or more mg, 4 or more mg, or 5 or more mg per day.

In some aspects of the invention, hydrocortisone is used in the combination treatments and co-formulations. Hydrocortisone is available from a number of sources including Pfizer (NY, N.Y.). In one embodiment, hydrocortisone is administered in an amount from about 20 mg to about 800 mg per day. In one aspect of this embodiment, hydrocortisone is administered in an amount from about 20 mg to about 700 mg, 20 mg to about 600 mg, 20 mg to about 500 mg, 20 mg to about 400 mg, or 20 mg to about 300 mg per day. In one aspect of this embodiment, hydrocortisone is administered in an amount from about 700 or less mg, 600 or less mg, 500 or less mg, 400 or less mg, 300 or less mg, or 200 or less mg day. In one aspect of this embodiment, hydrocortisone is administered in an amount from about 20 or more mg, 30 or more mg, 40 or more mg, 50 or more mg, 60 or more mg, or 70 or more mg day.

In some aspects of the invention, methylprednisolone is used in the combination treatments and co-formulations. Methylpredisolone is available from a number of sources including Par Pharmaceutical (Woodcliff Lake, N.J.). In one embodiment, methylprednisolone is administered in an amount from about 4 mg to about 160 mg per day. In one aspect of this embodiment, methylprednisolone is administered in an amount from about 4 mg to about 140 mg, 4 mg to about 120 mg, 4 mg to about 100 mg, or 4 mg to about 80 mg per day. In one aspect of this embodiment, methylprednisolone is administered in an amount from about 150 or less mg, 140 or less mg, 130 or less mg, 120 or less mg, 110 or less mg, or 100 or less mg per day. In one aspect of this embodiment, methylprednisolone is administered in an amount from about 4 or more mg, 10 or more mg, 20 or more mg, 30 or more mg, 40 or more mg, or 50 or more mg per day.

In some aspects of the invention, prednisolone is used in the combination treatments and co-formulations. Prednisolone is available from a number of sources including Par Pharmaceuticals (Woodcliff Lake, N.J.). In one embodiment, prednisolone is administered in an amount from about 5 mg to about 200 mg per day. In one aspect of this embodiment, prednisolone is administered 5 mg to about 180 mg, mg to about 150 mg, 5 mg to about 125 mg, or 5 mg to about 100 mg per day. In one aspect of this embodiment, prednisolone is administered in an amount from about 200 or less mg, 150 or less mg, 125 or less mg, 100 or less mg, 90 or less mg, or 80 or less mg per day. In one aspect of this embodiment, prednisolone is administered in an amount from about 5 or more mg, 10 or more mg, 20 or more mg, 30 or more mg, 40 or more mg, or 50 or more mg per day.

In some aspects of the invention, prednisone is used in the combination treatments and co-formulations. Prednisone is available from a number of sources including Watson Pharmaceuticals (Coronona, Calif.). In one embodiment, prednisone is administered in an amount from about 5 mg to about 200 mg per day. In one aspect of this embodiment, prednisone is administered 5 mg to about 180 mg, 4 mg to about 150 mg, 5 mg to about 125 mg, or 4 mg to about 100 mg per day. In one aspect of this embodiment, prednisone is administered in an amount from about 200 or less mg, 150 or less mg, 125 or less mg, 100 or less mg, 90 or less mg, or 80 or less mg per day. In one aspect of this embodiment, prednisone is administered in an amount from about 20 or more mg, 30 or more mg, 40 or more mg, 50 or more mg, 60 or more mg, or 70 or more mg per day.

In some aspects of the invention, triamcinolone is used in the combination treatments and co-formulations. Triamcinolone is available from a number of sources including Astellas Pharma (Deerfield, Ill.). In one embodiment, triamcinolone is administered in an amount from about 2 mg to about 60 mg per day. In one aspect of this embodiment, triamcinolone is administered 2 mg to about 50 mg, 2 mg to about 45 mg, 2 mg to about 35 mg, or 2 mg to about 30 mg per day. In one aspect of this embodiment, triamcinolone is administered in an amount from about 60 or less mg, 50 or less mg, 40 or less mg, 35 or less mg, 30 or less mg, or 25 or less mg per day. In one aspect of this embodiment, triamcinolone is administered in an amount from about 2 or more mg, 5 or more mg, 10 or more mg, 15 or more mg, 20 or more mg, or 25 or more mg day per day.

In some aspects of the invention, pregnenolone is used in the combination treatments and co-formulations. Pregnenolone is available from a number of sources and has a CAS number of [145-13-1]. In one embodiment, pregnenolone is administered in an amount from about 5 mg to about 1000 mg per day. In one aspect of this embodiment, pregnenolone is administered 5 mg to about 500 mg, 5 mg to about 400 mg, 5 mg to about 300 mg, or 5 mg to about 200 mg per day. In one aspect of this embodiment, pregnenolone is administered in an amount from about 200 or less mg, 150 or less mg, 125 or less mg, 100 or less mg, 90 or less mg, or 80 or less mg per day. In one aspect of this embodiment, pregnenolone is administered in an amount from about 20 or more mg, 30 or more mg, 40 or more mg, 50 or more mg, 75 or more mg, or 100 or more mg per day.

In some aspects of the invention DHEA (Dehydroepiandrosterone) is used in the combination treatments and co-formulations. DHEA is available from a number of sources and has a CAS number of [53-43-0]. In one embodiment, pregnenolone is administered in an amount from about 5 mg to about 300 mg per day. In one aspect of this embodiment, DHEA is administered 5 mg to about 250 mg, 5 mg to about 200 mg, mg to about 150 mg, or 5 mg to about 100 mg per day. In one aspect of this embodiment, DHEA is administered in an amount from about 200 or less mg, 150 or less mg, 125 or less mg, 100 or less mg, 90 or less mg, or 80 or less mg per day. In one aspect of this embodiment, prednisone is administered in an amount from about 20 or more mg, 30 or more mg, 40 or more mg, 50 or more mg, 75 or more mg, or 100 or more mg per day.

In some aspects of the invention 7beta-hydroxy epiandrosterone is used in the combination treatments and co-formulations. 7beta-hydroxy epiandrosterone is available from a number of sources. In one embodiment 7beta-hydroxy epiandrosterone is administered in an amount from about 5 mg to about 1000 mg per day. In one aspect of this embodiment, 7beta-hydroxy epiandrosterone is administered mg to about 500 mg, 5 mg to about 400 mg, 5 mg to about 300 mg, or 5 mg to about 200 mg per day. In one aspect of this embodiment, 7beta-hydroxy epiandrosterone is administered in an amount from about 200 or less mg, 150 or less mg, 125 or less mg, 100 or less mg, 90 or less mg, or 80 or less mg per day. In one aspect of this embodiment, 7beta-hydroxy epiandrosterone is administered in an amount from about 20 or more mg, 30 or more mg, 40 or more mg, 50 or more mg, 75 or more mg, or 100 or more mg per day.

The invention further provides additional combination therapy strategies for treating traumatic brain injuries (TBI) or related disorders. According to this aspect of the invention, an individual in need of treatment is administered an effective amount of (1) one or more Abeta42 lowering agents, (2) one or more steroidal agents, and (3) one or more compounds selected from the group consisting of NSAIDs, acetylcholine esterase inhibitors (e.g., donepezil, galantamine, rivastagmine), COX-2 inhibitors (cyclooxygenase-2), beta-secretase inhibitors, gamma-secretase inhibitors, NMDA antagonists (i.e., memantine), and GABA-A alpha inverse agonist (see WO 00/27382, WO 96/25948, WO 98/50385 which are herein incorporated by reference in there entireties). NMDA receptor antagonists for combination therapy are memantine, adamantane, amantadine, an adamantane derivative, dextromethorphan, dextrorphan, dizocilpine, ibogaine, ketamine, and remacemide. The invention further encompasses compositions comprising the combination of active ingredients of this aspect of the invention.

The amount, timing and mode of delivery of compositions of the invention comprising an effective amount of a psychotherapeutic compound and an effective amount of opipramol will be routinely adjusted on an individual basis, depending on such factors as weight, age, gender, and condition of the individual, the acuteness of the targeted traumatic brain injuries (TBI) or related disorders and/or related symptoms, whether the administration is prophylactic or therapeutic, and on the basis of other factors known to effect drug delivery, absorption, pharmacokinetics, including half-life, and efficacy.

In some embodiments, the compositions and formulations of the present invention may be administered according to a flexible dosing regimen. The treatment regimen provides for dosing periods during which a sufficient number of doses of the compositions and formulations of the present invention are administered to provide relief from traumatic brain injuries (TBI) or related disorder symptoms. The one or more embodiments herein provides for dosing according to a discontinuous schedule. In a discontinuous schedule, each dosing period is followed by an evaluation period, during which the user can self-evaluate the occurrence and severity of symptoms. If the user determines that it is necessary to begin a new dosing period, the user may do so at any time following this evaluation period. If, however, the user feels the need to begin a new dosing period before the evaluation period has passed, or to take more than the recommended number of doses, then the user may, for example, choose to seek professional medical advice.

An effective dose or multi-dose treatment regimen for the psychotherapeutic compounds of the invention will ordinarily be selected to approximate a minimal dosing regimen that is necessary and sufficient to substantially prevent or alleviate one or more symptom(s) of the targeted traumatic brain injuries (TBI) or related disorders as described herein. For example, opipramol may be administered in dosages ranging from 5 to 500 mg one or more times per day, from 25 to 450 mg per day, from 50 to 400 mg per day, from 50 to 350 mg per day, or from 50 to 300 mg per day. Typically, opipramol will be administered bi-daily. In some embodiments, sub-therapeutic amounts may be used. Exemplary suggested dosage ranges for selected drugs for use within certain embodiments of the invention are provided below, for illustrative purposes. Additional exemplary dosage ranges are provided below for selected drugs formulated for sustained delivery within additional embodiments of the invention, also for illustrative purposes.

These and other effective unit dosage amounts of either or both of the psychotherapeutic agent and/or opipramol may be administered in a single dose, or in the form of multiple daily, weekly or monthly doses, for example in a dosing regimen comprising from 1 to 5, or 2-3, doses administered per day, per week, or per month. In exemplary embodiments, exemplary dosages of selected drugs as illustrated above are administered one, two, three, or four times per day. In more detailed embodiments, specific dosages within the specified exemplary ranges above are administered once, twice, or three times daily. In alternate embodiments, dosages are calculated based on body weight, and may be administered, for example, in amounts as exemplified above adjusted for body weight.

In more detailed embodiments of the invention, the sustained release compositions and dosage forms will yield a therapeutic level of an active therapeutic agent following administration to a mammalian subject in a desired dosage amount (e.g., 25, 50, 100, 150, 200, 250, 300, 350, 400, 450 or 500 mg) that yields a minimum plasma concentration of at least a lower end of a therapeutic dosage range as exemplified herein over a period of at least about 6 hours, at least about 8 hours, at least about 12 hours, at least about 18 hours, or up to 24 hours or longer. In alternate embodiments of the invention, the sustained release compositions and dosage forms will yield a therapeutic level of active therapeutic agent following administration to a mammalian subject in a desired dosage amount (e.g., 25, 50, 100, 150, 200, 250, 300, 350, 400, 450 or 500 mg) that yields a minimum plasma concentration that is known to be associated with clinical efficacy, over a period of at least about 6 hours, at least about 8 hours, at least about 12 hours, at least about 18 hours, or up to 24 hours or longer.

In certain embodiments, the active therapeutic agent is/are released from the compositions and dosage forms of the invention and delivered into the blood plasma or other target site of activity in the subject in a sustained release profile characterized in that from about 0% to 20% of the active compound is released and delivered (as determined, e.g., by measuring blood plasma levels) within in 0 to 2 hours, from 20% to 50% of the active compound is released and delivered within about 2 to 12 hours, from 50% to 85% of the active compound is released and delivered within about 3 to hours, and greater than 75% of the active compound is released and delivered within about 5 to 18 hours.

Pharmaceutical dosage forms of a compound of the present invention may optionally include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

The compositions of the invention for treating traumatic brain injuries (TBI) or related disorders, can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

By "pharmaceutically acceptable carrier" is meant any diluent or excipient that is compatible with the other ingredients of the formulation, and which is not deleterious to the recipient. The pharmaceutically acceptable carrier can be selected on the basis of the desired route of administration, in accordance with standard pharmaceutical practices. Pharmaceutical compositions of the invention for parenteral administration can take the form of an aqueous or nonaqueous solution, dispersion, suspension or emulsion. In preparing pharmaceutical compositions of the invention for parenteral administration, opipramol can be mixed with a suitable pharmaceutically acceptable carrier such as water, oil (particularly a vegetable oil), ethanol, saline solutions (e.g., normal saline), aqueous dextrose (glucose) and related sugar solutions, glycerol, or glycols such as propylene glycol or polyethylene glycol. Pharmaceutical compositions of the invention for parenteral administration preferably contain a water-soluble salt of opipramol. Stabilizing agents, antioxidizing agents and preservatives can also be added to the pharmaceutical compositions for parenteral administration. Suitable antioxidizing agents include sulfite, ascorbic acid, citric acid and its salts, and sodium EDTA. Suitable preservatives include benzalkonium chloride, methyl- or propyl-paraben, and chlorbutanol.

In preparing pharmaceutical compositions of the invention for oral administration, opipramol can be combined with one or more solid or liquid inactive ingredients to form tablets, capsules, pills, powders, granules or other suitable oral dosage forms. For example, opipramol can be combined with at least one pharmaceutically acceptable carrier such as a solvent, filler, binder, humectant, disintegrating agent, solution retarder, absorption accelerator, wetting agent absorbent or lubricating agent. In one embodiment, opipramol is combined with carboxymethylcellulose calcium, magnesium stearate, mannitol or starch, and is formed into tablets by conventional tableting methods.

Pharmaceutical compositions of the invention can be formulated so as to provide buccal absorption including thin film formulations and orally dissolving tablets to provide faster absorption than the oral/GI route and to bypass first-pass hepatic metabolism of opipramol by cytochrome P-450 3A4 as a CYP3A substrate. Preferably, a controlled-release pharmaceutical composition of the invention is capable of releasing opipramol into a subject at a rapid onset, so as to maintain a substantially constant or desired pharmacological activity for a given period of time, reduce or remove the effect of food on absorption, and to provide elimination of the drug and metabolites from the body with a reduced terminal elimination phase.

Pharmaceutical compositions of the invention can also be formulated so as to provide controlled-release of opipramol upon administration of the composition to a subject. Preferably, a controlled-release pharmaceutical composition of the invention is capable of releasing opipramol into a subject at a desired rate, so as to maintain a substantially constant or desired pharmacological activity for a given period of time. As used herein, a "controlled-release component" is a compound such as a lipid or mixture of lipids, liposome and/or microsphere that induces the controlled-release of opipramol into the subject upon exposure to a certain physiological compound or condition. For example, the controlled-release component can be biodegradable, activated by exposure to a certain pH or temperature, by exposure to an aqueous environment, or by exposure to enzymes.

Formulation of controlled-release pharmaceutical compositions of the invention is within the skill in the art. Controlled release formulations suitable for use in the present invention are described in, for example, U.S. Pat. No. 5,674,533 (liquid dosage forms), U.S. Pat. No. 5,591,767 (liquid reservoir transdermal patch), U.S. Pat. No. 5,120,548 (device comprising swellable polymers), U.S. Pat. No. 5,073,543 (ganglioside-liposome vehicle), U.S. Pat. No. 5,639,476 (stable solid formulation coated with a hydrophobic acrylic polymer), the entire disclosures of which are herein incorporated by reference.

Biodegradable microparticles can also be used to formulate controlled-release pharmaceutical compositions suitable for use in the present invention, for example as described in U.S. Pat. Nos. 5,354,566 and 5,733,566, the entire disclosures of which are herein incorporated by reference.

In one embodiment, controlled-release pharmaceutical compositions of the invention comprise opipramol and a controlled-release component. As used herein, a "controlled-release component" is a compound such as a polymer, polymer matrix, gel, permeable membrane, liposome and/or microsphere that induces the controlled-release of opipramol into the subject upon exposure to a certain physiological compound or condition. For example, the controlled-release component can be biodegradable, activated by exposure to a certain pH or temperature, by exposure to an aqueous environment, or by exposure to enzymes. An example of a controlled-release component which is activated by exposure to a certain temperature is a sol-gel. In this embodiment, opipramol is incorporated into a sol-gel matrix that is a solid at room temperature. This sol-gel matrix is implanted into a subject having a body temperature high enough to induce gel formation of the sol-gel matrix, thereby releasing the active ingredient into the subject.

In one embodiment, pharmaceutical compositions of the invention may comprise opipramol and components that form micelles. Micelles containing opipramol in the stomach and proximal small intestine facilitate absorption. Example of a micelle-component which is activated by exposure to a certain temperature is found in U.S. Pat. Nos. 6,761,903; 6,720,001; 6,383,471; 6,309,663; 6,267,985; and 6,248,363, incorporated herein by reference. In this embodiment, opipramol is incorporated into a soft-gel capsule. Such components may mimic the augmentation of absorption termed the "food effect", and such formulations may provide more predictable absorption by eliminating the "food effect" from dietary sources.

The composition of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

The magnitude of a prophylactic or therapeutic dose of the active ingredient (i.e., opipramol or metabolite thereof) in the prevention or treatment of a human will vary with the type of affliction, the severity of the patient's affliction and the route of administration. The dose and dose frequency will also vary according to the age, weight and response of the individual patient. However, the dosage will not equal or exceed 500 mgs per day. In a preferred embodiment, one dose is given at bed time or up to several hours before bedtime to facilitate the achievement of deep, refreshing sleep. Bedtime may be any hour of the day at which a person engages in the most extensive period of sleep.

Any of the methods of treatment described above may be combined with psychotherapeutic intervention to improve the outcome of the treatment including: psychological debriefing, cognitive behavior therapy and eye movement desensitization and reprocessing, systematic desensitization, relaxation training, biofeedback, cognitive processing therapy, stress inoculation training, assertiveness training, exposure therapy, combined stress inoculation training and exposure therapy, combined exposure therapy and relaxation training and cognitive therapy.

An active therapeutic agent of the present invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets and capsules, which may be prepared by any conventional method of preparing pharmaceutical oral unit dosage forms can be utilized in preparing oral unit dosage forms. Oral unit dosage forms, such as tablets or capsules, may contain one or more conventional additional formulation ingredients, including, but are not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate. Such rapidly acting dosage forms would be useful, for example, in the prevention or treatment of acute attacks of panic disorder.

The active therapeutic agent of the invention can be prepared and administered in any of a variety of delivery forms known in the art. Compositions and methods of the invention are provided for topical administration of an active therapeutic agent of the present invention for treating traumatic brain injuries (TBI) or related disorders. Topical compositions may comprise a compound of the present invention and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a compound of the present invention dissolved or dispersed in water or other solvent or liquid to be incorporated in the topical composition or delivery device. It can be readily appreciated that the transdermal route of administration may be enhanced by the use of various dermal penetration enhancers known to those skilled in the art. Formulations suitable for such dosage forms incorporate excipients commonly utilized therein, particularly means, e.g., structure or matrix, for sustaining the absorption of the drug over an extended period of time, for example 24 hours. A once-daily transdermal patch will be particularly useful for patients suffering from or at risk for selected traumatic brain injuries (TBI) or related disorders, such as generalized anxiety disorder, acute stress disorder or PTSD.

Use of transdermal delivery devices and methods is particularly advantageous for administration of opipramol within the present invention. Transdermal administration of opipramol may provide several advantages over oral delivery, including improved patient compliance and responsivity, bypass of first-pass metabolism, sustained drug delivery, and minimal variability both within and between patients. The properties of opipramol indicate that it is suitable for formulation in a transdermal patch.

A matrix-type transdermal patch may be effective for opipramol treatment of traumatic brain injuries (TBI) or related disorders. The dose of opipramol delivered by transdermal patch will typically range from 5-500 mg per day, from 25 to 450 mg per day, from 40 to 450 mg per day, from 50 to 400 mg per day, from 50 to 300 mg per day, from 100 to 300 mg per day, from 150 to 300 mg per day, as determined by the prescribing physician in light of such ordinary dosing factors as patient condition, body weight, duration of treatment, etc. Transdermal patch delivery devices and methods of the invention will yield increased opipramol bioavailability compared to oral administration of an equivalent opipramol dose. In particular, a transdermal patch will result in a 20-50% bioavailability increase, more typically a 50%-100% increase, up to a two-fold, three-fold, or greater increase, and as much as a five-fold or greater increase in bioavailability compared to that obtained with an equivalent oral dosage form (e.g., an IR or SR capsule or tablet form). The pharmacokinetic properties of oral and transdermal patch delivered opipramol can be measured as described in Example 6. Within more detailed aspects of the invention, transdermal delivery devices and methods for delivering opipramol and other therapeutic compounds as described herein will yield approximately zero-order kinetics, to provide steady state levels of the active drug within 24 hours, and to reduce peak to trough ratios of drug levels (e.g., reduced Cmax/Cmin) in comparison to oral delivery, to yield more continuous therapeutic exposure.

Transdermal delivery systems useful for the compositions and methods of the present invention are typically fabricated as multilayered polymeric laminates in which a drug reservoir or a drug-polymer matrix is sandwiched between two polymeric layers: an outer impervious backing layer that creates an occlusive environment and prevents the loss of drug through the backing surface and an inner polymeric layer that functions as an adhesive and/or rate-controlling membrane. In the case of a drug reservoir design, the reservoir is sandwiched between the backing and a rate controlling membrane. The drug releases only through the rate-controlling membrane, which can be microporous or nonporous. In the drug reservoir compartment, the drug can be in the form of a solution, suspension, or gel or dispersed in a solid polymer matrix. On the outer surface of the polymeric membrane a thin layer of drug-compatible, hypoallergenic adhesive polymer may be applied.

For the drug matrix design, two general types of system include the drug-in-adhesive system and the matrix dispersion system. In the drug-in-adhesive system, the drug reservoir is formed by dispersing the drug in an adhesive polymer and then spreading the medicated polymer adhesive by solvent casting or by melting the adhesive (in the case of hot-melt adhesives) onto an impervious backing layer. On top of the reservoir, layers of unmedicated adhesive polymer are applied. In the case of the matrix dispersion system, the drug is dispersed homogeneously in a hydrophilic or lipophilic polymer matrix and fixed onto a drug-impermeable backing layer by solvent casting or extrusion. Instead of applying the adhesive on the face of the drug reservoir, it is applied to form a peripheral adhesive. Illustrative examples of suitable adhesives as matrix type delivery systems include those described in U.S. Pat. Nos. 5,474,783, and 5,656,386. Other transdermal systems include films, plasters, dressings, and bandages, as well as multilayer delivery systems in which the drug is solubilized or contained in one or more separate layers, and reservoir-type delivery systems in which the drug is solubilized or contained in a reservoir or depot separate from the adhesive which attaches directly to the skin or mucosa.

Suitable adhesives for transdermal patches are known in the art and include pressure-sensitive adhesives and bioadhesives. Pressure sensitive adhesives suitable for use in accordance with the invention include, but are not limited to, pressure-sensitive silicone adhesives, pressure-sensitive acrylic adhesives, and mixtures of any two or more thereof. Exemplary pressure-sensitive silicone adhesives include polysiloxanes and other silicone adhesives as disclosed in U.S. Pat. Nos. 4,591,622; 4,584,355; 4,585,836; 4,655,767; and 5,958,446. Suitable silicone pressure-sensitive adhesives are commercially available and include the silicone adhesives sold under the trademarks BIO-PSA X7-3027. BIO-PSA X7-4919, BIO-PSA X7-2685, and BIO-PSA X7-3122 by Dow Corning Corporation, Medical Products, Midland, Mich.

Bioadhesive materials useful in some embodiments include those described in U.S. Pat. No. 6,562,363. For example, bioadhesive materials may include polymers, either water soluble or water insoluble, with or without crosslinking agents, which are bioadhesive. Exemplary bioadhesives include natural materials, cellulose materials, synthetic and semi-synthetic polymers, and generally, any physiologically acceptable polymer showing bioadhesive properties, or mixtures of any two or more thereof.

Suitable acrylic-based pressure-sensitive adhesives for transdermal patches are also known in the art. Such acrylic-based polymers may be used as the primary pressure-sensitive adhesive (see, e.g., U.S. Pat. No. 4,390,520), or may be used in combination with other polymers which may or may not be pressure-sensitive adhesives (see, e.g., U.S. Pat. No. 4,994,267). Acrylic-based pressure-sensitive adhesives may be polymerized with functional monomers to provide functional groups on the acrylic-based adhesive, such as may be desired to improve wear properties and drug delivery. Suitable polyacrylic acid polymers include polymers of acrylic acid crosslinked with polyalkenenyl ethers (generically known as carbomers) or divinyl glycol (generically known as polycarbophils).

Polymer blends as described in U.S. Pat. No. 5,958,446 may also be used as pharmaceutically acceptable carriers and adhesives in the transdermal compositions embodied herein.

In certain embodiments of transdermal patches used in the compositions of the invention, a plasticizer or tackifying agent is incorporated into the formulation to improve the adhesive characteristics of the composition. A tackifying agent is particularly useful in those embodiments in which the drug does not plasticize the polymer. Suitable tackifying agents are those known in the art including: (1) aliphatic hydrocarbons; (2) mixed aliphatic and aromatic hydrocarbons; (3) aromatic hydrocarbons; (4) substituted aromatic hydrocarbons; (5) hydrogenated esters; (6) polyterpenes; and (7) hydrogenated wood rosins. The tackifying agent employed is preferably compatible with the blend of polymers. In some embodiments, the tackifying agent is silicone fluid (e.g., 360 Medical Fluid, available from Dow Corning Corporation, Midland, Mich.) or mineral oil. Silicone fluid is useful for blends comprising polysiloxane as a major component. In other embodiments, where polyacrylate, for example, is a major component, mineral oil may be used as a tackifying agent.

Transdermal patch compositions may also contain agents known to accelerate the delivery of the drug through the skin. Such agents have been referred to as skin-penetration enhancers, accelerants, adjuvants, and sorption promoters. This class of agents includes those with diverse mechanisms of action including those which have the function of improving the solubility and diffusibility of the drug within the multiple polymer and those which improve percutaneous absorption, for example, by changing the ability of the stratum corneum to retain moisture, softening the skin, improving the skin's permeability, acting as penetration assistants or hair-follicle openers or changing the state of the skin including the boundary layer. Some of these agents have more than one mechanism of action, but in essence they serve to enhance the delivery of the drug. Some exemplary agents are listed in U.S. Pat. Nos. 5,958,446 and 6,562,363.

The topical or transdermal compositions of the present invention can be made in accordance with methods known in the art. For example, opipramol can be blended with the pharmaceutically acceptable topical or transdermal carrier components, or by dissolving the opipramol in a solvent and combining the solution with the pharmaceutically acceptable topical or transdermal carrier components, or by other conventional methods. In the case of a transdermal patch, the substrate is laminated to one or more additional layers, such as a protective layer, a backing layer, a rate-controlling layer, a membrane layer, or one or more other types of layers known in the art.

The pharmaceutical compositions and dosage forms of the current invention will typically be provided for administration in a sterile or readily sterilizable, biologically inert, and easily administered form.

Also contemplated within the present disclosure is the use of compositions described herein as a preventive or prophylactic measure against a traumatic brain injury such as concussion. In some embodiments, the compositions are administered to a subject prior to a traumatic brain injury. The disclosure also includes methods for treating subjects who are at risk of a traumatic brain injury or who have previously suffered from a traumatic brain injury comprising administering to the subjects an effective amount of the compositions described herein. In other embodiments, the compositions are used for treating a subject who is suspected of having a traumatic brain injury or a subject who may have suffered from a traumatic brain injury. The subject may or may not display symptoms of a traumatic brain injury.

In other embodiments the invention provides pharmaceutical kits for reducing, treating, preventing or alleviating symptoms in a human subject suffering from or at risk for a traumatic brain injuries (TBI) or related disorders. The kits comprise an active therapeutic agent in an effective amount, and a container means for containing the active therapeutic agent for coordinate administration to the subject (for example a container, divided bottle, or divided foil pack). The container means can include a package bearing a label or insert that provides instructions for multiple uses of the kit contents to treat the traumatic brain injuries (TBI) or related disorders and reduce symptoms in the subject. In more detailed embodiments, the active therapeutic agent is admixed or co-formulated in a single, combined dosage form, for example a liquid or solid oral dosage form. In alternate embodiments, the active therapeutic agents are contained in the kit in separate dosage forms for coordinate administration. Other variations of memory aids will be readily apparent.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A method of treating post-concussive syndrome in a human subject who has sustained a concussion, comprising:

administering to the human subject a therapeutically effective amount of a pharmaceutical composition comprising opipramol, wherein the post-concussive syndrome comprises at least one symptom selected from anxiety, irritability, cognitive dysfunction, insomnia, sleep disturbance, difficulty concentrating, difficulty remembering, fatigue, drowsiness, or a combination thereof, wherein the administering ameliorates the at least one symptom, and wherein the administering is initiated within seven days of the concussion or within seven days of appearance of the at least one symptom.

2. The method of claim 1, wherein the administering is performed at least once daily.

3. The method of claim 1, wherein the administering comprises orally administering the pharmaceutical composition.

4. The method of claim 1, wherein the pharmaceutical composition comprises one or more pharmaceutically acceptable carriers or excipients.

5. A method of treating post-concussive syndrome in a human subject who has sustained a concussion, comprising:

sublingually administering to the human subject a therapeutically effective amount of a pharmaceutical composition comprising opipramol, wherein the post-concussive syndrome comprises at least one symptom selected from anxiety, irritability, cognitive dysfunction, insomnia, sleep disturbance, difficulty concentrating, difficulty remembering, fatigue, drowsiness, or a combination thereof, wherein the sublingual administration ameliorates the at least one symptom, and wherein the sublingual administration is initiated within seven days of the concussion or within seven days of appearance of the at least one symptom.

6. The method of claim 5, wherein the sublingual administration is performed at least once daily.

7. The method of claim 5, wherein the pharmaceutical composition comprises one or more pharmaceutically acceptable carriers or excipients.

8. The method of claim 5, wherein the opipramol is administered in an amount from about 0.2 mg/kg per day to about 200 mg/kg per day.

9. The method of claim 5, wherein opipramol is the only therapeutically active agent in the pharmaceutical composition.

* * * * *